United States Patent [19]

Zupkas et al.

[11] Patent Number: 4,737,139
[45] Date of Patent: * Apr. 12, 1988

[54] UNITARY VENOUS RETURN RESERVOIR WITH CARDIOTOMY FILTER

[75] Inventors: Paul F. Zupkas, Costa Mesa; Francis M. Servas, San Juan Capistrano; Todor Pavlov, Laguna Niguel; Steven G. Kelly, Garden Grove, all of Calif.

[73] Assignee: Shiley Inc., Irvine, Calif.

[*] Notice: The portion of the term of this patent subsequent to Feb. 10, 2004 has been disclaimed.

[21] Appl. No.: 12,411

[22] Filed: Feb. 9, 1987

Related U.S. Application Data

[63] Continuation of Ser. No. 696,147, Jan. 29, 1985, Pat. No. 4,642,087.

[51] Int. Cl.$^4$ ............................................. A61M 37/00
[52] U.S. Cl. ........................................... 604/4; 604/51; 128/DIG. 3; 55/178; 210/256; 210/438; 210/458
[58] Field of Search ........................................ 604/4–7, 604/51–53; 128/DIG. 3; 55/178; 210/256, 315, 436, 438, 440, 439, 443, 458, 927, DIG. 13

[56] References Cited

U.S. PATENT DOCUMENTS

| | | | |
|---|---|---|---|
| 3,507,395 | 4/1970 | Bentley | 604/4 |
| 3,775,339 | 11/1973 | Kasulin et al. | 55/178 |
| 3,891,416 | 6/1975 | Leonard et al. | 55/178 |
| 3,993,461 | 11/1976 | Leonard et al. | 55/178 |
| 4,054,523 | 10/1977 | Ingenito et al. | 210/188 |
| 4,094,791 | 6/1978 | Conrad | 210/DIG. 13 |
| 4,344,777 | 8/1982 | Siposs | 55/178 |
| 4,490,331 | 12/1984 | Steg, Jr. | 128/DIG. 3 |
| 4,642,089 | 2/1987 | Zupkas et al. | 128/DIG. 3 |

FOREIGN PATENT DOCUMENTS

| | | | |
|---|---|---|---|
| 0114732 | 8/1984 | European Pat. Off. | 604/4 |
| 0122748 | 10/1984 | European Pat. Off. | 604/4 |

*Primary Examiner*—C. Fred Rosenbaum
*Assistant Examiner*—Mario Costantino
*Attorney, Agent, or Firm*—P. C. Richardson; L. C. Akers; R. C. Turner

[57] ABSTRACT

A unitary device for the treatment and collection of blood from two different sources during a surgical procedure comprises a hollow housing made of a rigid, preferably transparent, material, first and second blood inlets in the housing, a first blood treatment element inside the housing comprising a layer of porous defoaming material and a layer of non-woven depth filter material, and a second blood treatment element inside the housing comprising a layer of porous defoaming material and free of any depth filter material. The novel device also includes internal walls for providing two blood flow paths therein, one through the first inlet, the first blood treatment element, a blood collection reservoir defined within the device and a treated blood outlet in the bottom wall of the housing, and the other through the second inlet, the second blood treatment element, the blood collection reservoir and the blood outlet. The latter blood flow path bypasses at least the depth filter material layer of the first blood treatment element. In typical use in an extracorporeal flow circuit, cardiotomy blood is introduced to the first inlet, venous return blood is introduced to the second inlet and the common blood outlet is connected to an extracorporeal blood pump. As a result, passage of the relatively clean venous return blood through a depth filter material is avoided.

7 Claims, 2 Drawing Sheets

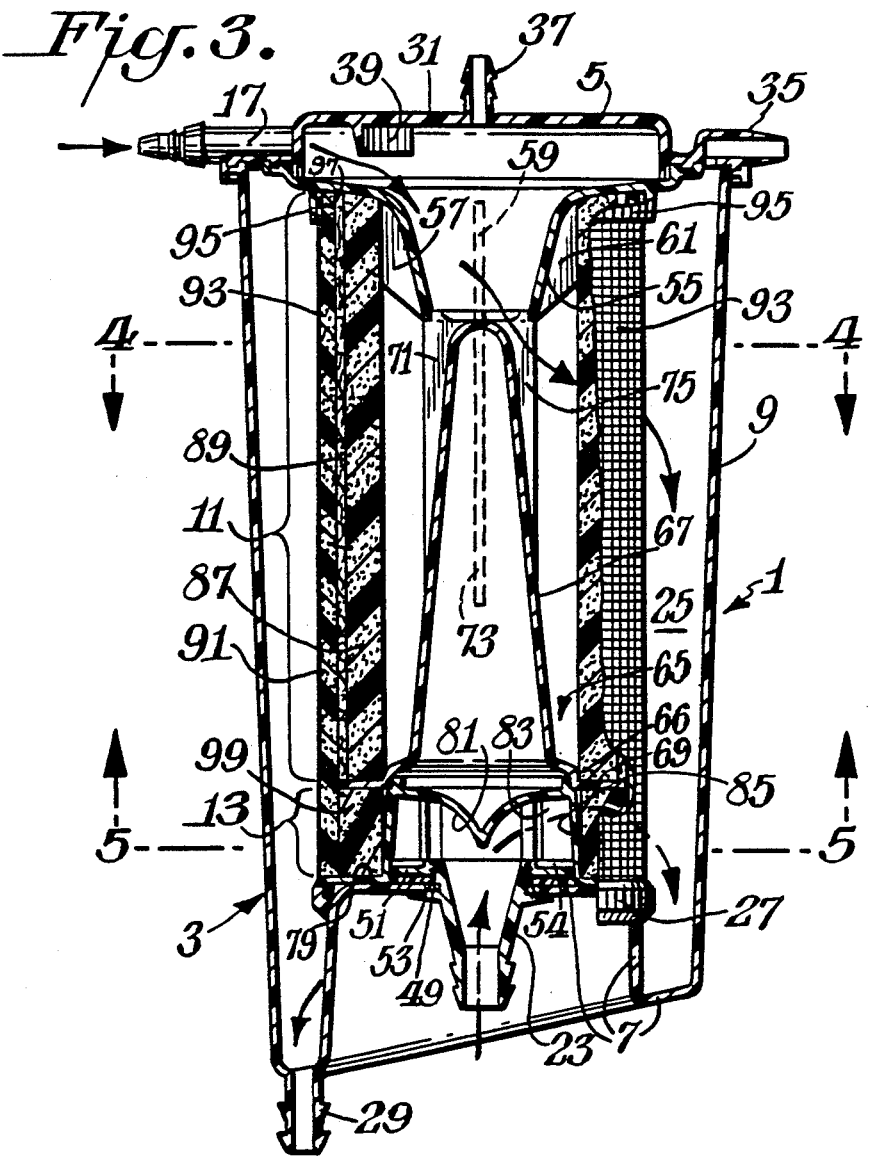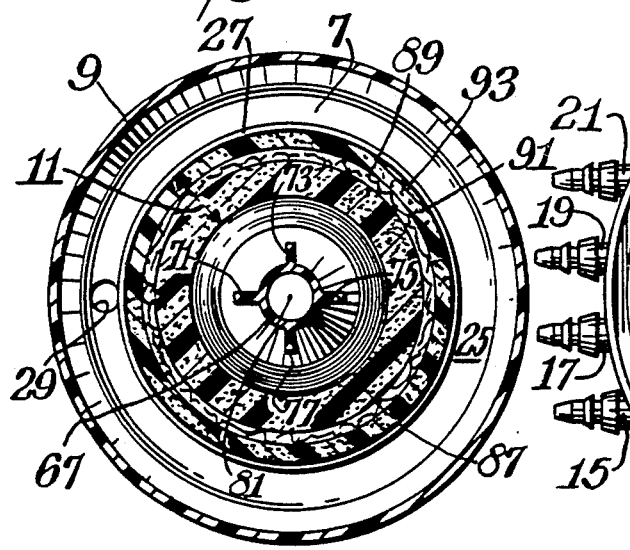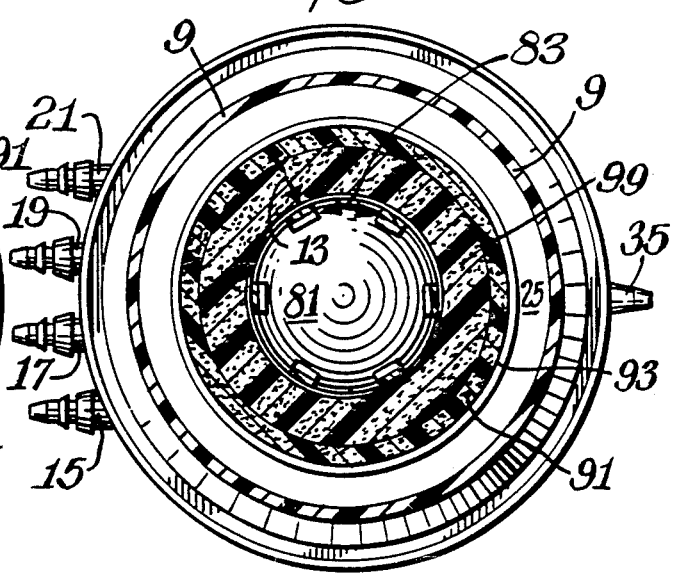

UNITARY VENOUS RETURN RESERVOIR WITH CARDIOTOMY FILTER

This is a continuation of application Ser. No. 696,147, filed on Jan. 29, 1985, now U.S. Pat. No. 4,642,087.

BACKGROUND OF THE INVENTION

In a number of surgical procedures referred to in the art as cardiopulmonary bypass operations, it is necessary to interrupt and suspend the normal functioning of the patient's heart and lungs and to temporarily replace the function of these organs with artificial blood handling and treating units in a lifesustaining extracorporeal blood flow circuit. In these procedures the main body of the patient's blood, which is called the venous return stream, is typically withdrawn from the patient through a venous cannula inserted into the right atrium, collected in a venous reservoir, and then passed through a blood pump (artificial heart), blood oxygenator (artificial lung) and arterial blood filter before being returned to the patient through an aortic cannula inserted into the aorta distal to the aortic arch. In conventional practice, the venous reservoir is a flexible transparent bag with a blood outlet in the bottom. Additionally, in typical practice, patient's blood from the surgical field, which is called cardiotomy blood, is gathered in one or more cardiac vacuum suckers and defoamed, filtered and collected in a cardiotomy reservoir and filter device. The treated cardiotomy blood is then conducted to the venous reservoir, where it is combined with the venous return blood. A highly effective cardiotomy reservoir and filter device is disclosed in the copending, commonly assigned, U.S. patent application Ser. No. 483,375, filed Apr. 8, 1983.

Typically, the volume flow rate of the venous return blood is at least three times that of the total cardiotomy blood. The cardiotomy blood can be quite "dirty", containing gas bubbles, fragments of tissue, bone chips, blood clots, surgical debris, etc. Thus, cardiotomy reservoir/filter devices usually include in the blood flow path a layer of a porous defoaming material and a layer of a depth filter material for filtering out particulate matter. By contrast, the venous return blood is a much cleaner stream.

The type of extracorporeal blood treatment circuit described above has been used for many years with great success in cardiopulmonary bypass and related surgical procedures. Nevertheless, improvements in circuit and equipment design are constantly being sought. In particular, it would be highly desirable to replace the venous reservoir and cardiotomy reservoir/filter units, two separate pieces of equipment, with a single unitary piece of equipment in order to reduce equipment costs and necessary inventory levels, reduce required priming volumes, simplify the steps of assembling, operating and disassembling the extracorporeal circuit, and reduce the possibilities of making incorrect connections between pieces of equipment. It is not, however, feasible to pass both the venous return blood and the cardiotomy blood through a cardiotomy reservoir/filter of conventional design along the same flow path, because excessive pressure drops and/or equipment sizes would have to be employed. Furthermore, it is not necessary to filter the relatively clean venous return blood through a depth filter material. In fact, such a filtering step should normally be avoided because it would subject the venous return blood to significant shear stresses, and thus some risk of damage to blood constituents, with little concomitant benefit.

SUMMARY OF THE INVENTION

It is an object of the present invention to provide a unitary device for the treatment and collection of venous return and cardiotomy blood in extracorporeal circuits, which unitary device is capable of replacing separate venous reservoir and cardiotomy reservoir/filter units. This and other objects of the invention are achieved with a novel device for the treatment and collection of blood from two different sources during a surgical procedure comprising a hollow housing made of a rigid material and having a top wall, a side wall and a bottom wall; a first blood treatment element inside the housing comprising in series a layer of porous defoaming material and a layer of non-woven depth filter material; a second blood treatment element inside the housing comprising a layer of porous defoaming material, with the layer of depth filter material in the first element having a smaller mean pore size than both of said layers of defoaming material in the first and second elements and with the second blood treatment element being free of any depth filter material; a reservoir defined within the device for collecting treated blood; a gas vent in the top wall of the housing in communication with the reservoir; a treated blood outlet in the bottom wall of the housing at the bottom of the reservoir; first and second blood inlets in the housing; and means within the housing for providing a first blood flow path in the device through the first inlet, the first blood treatment element, said reservoir and said treated blood outlet and a second blood flow path in the device through the second inlet, the second blood treatment element, said reservoir and said treated blood outlet, with said means positively preventing blood in the second flow path from passing through the layer of non-woven depth filter material in the first blood treatment element. When cardiotomy blood is introduced into the first blood inlet and venous return blood into the second blood inlet, the cardiotomy blood is defoamed and filtered through a non-woven depth filter material in the first blood treatment element, while the venous return blood is defoamed, but not filtered through a depth filter material, in the second blood treatment element. After passing through their respective blood treatment elements the two blood flow streams are combined and collected in the common treated blood reservoir and then withdrawn from the device (for conduction to e.g. an extracorporeal blood pump) through the common blood outlet.

The device of the invention has many advantageous features. The functions of prior art venous reservoir and cardiotomy reservoir/filter units are combined in a single unitary device which can be of compact size and shape, be easy to assemble and operate, and require a relatively low volume of liquid for priming purposes. The novel device includes the facility to defoam the venous blood, which is lacking in conventional flexible bag venous reservoirs, but unnecessary and potentially traumatic passage of the venous return blood through a depth filter material is avoided.

In a preferred embodiment of the invention, the first and second blood treatment elements are both annular in shape and disposed in a vertically-extending manner inside the housing with the second element located directly below the first element. The side wall of the rigid housing is generally cylindical in shape and spaced radially from the two blood treatment elements. The first and second blood inlets communicate respectively with the inner spaces within the first and second blood treatment elements, and an internal wall within the device prevents liquid flow between these two inner spaces and prevents the blood in the second blood flow path from flowing through the layer of nonwoven depth filter material in the first blood treatment element. More preferably, at least the side wall of the rigid housing is transparent so that the level of treated blood in the reservoir can be readily observed during operation of the device. Most preferably, said side wall is provided with a graduated scale of markings to indicate the volume of treated blood in the reservoir. Accurate estimations of the volume of blood in conventional venous reservoirs during surgical procedures from the height of the blood level therein are rendered quite difficult by the flexible nature of these reservoirs.

The present invention also comprises a method for using the novel device of the invention to treat and combine blood from a first source and a second source during a surgical procedure.

DETAILED DESCRIPTION OF THE INVENTION

The invention will be described in detail with reference to a preferred embodiment thereof, which is a disposable blood treatment and collection device for use in an extracorporeal blood flow circuit, and its method of use. Reference to this embodiment does not limit the scope of the invention, which is limited only by the scope of the claims.

In the drawings:

FIG. 3 is a partial sectional view taken along line 3—3 in FIG. 1;

FIG. 4 is a sectional view taken along line 4—4 in FIG. 3; and

FIG. 5 is a sectional view taken along line 5—5 in FIG. 3.

Figure 1:
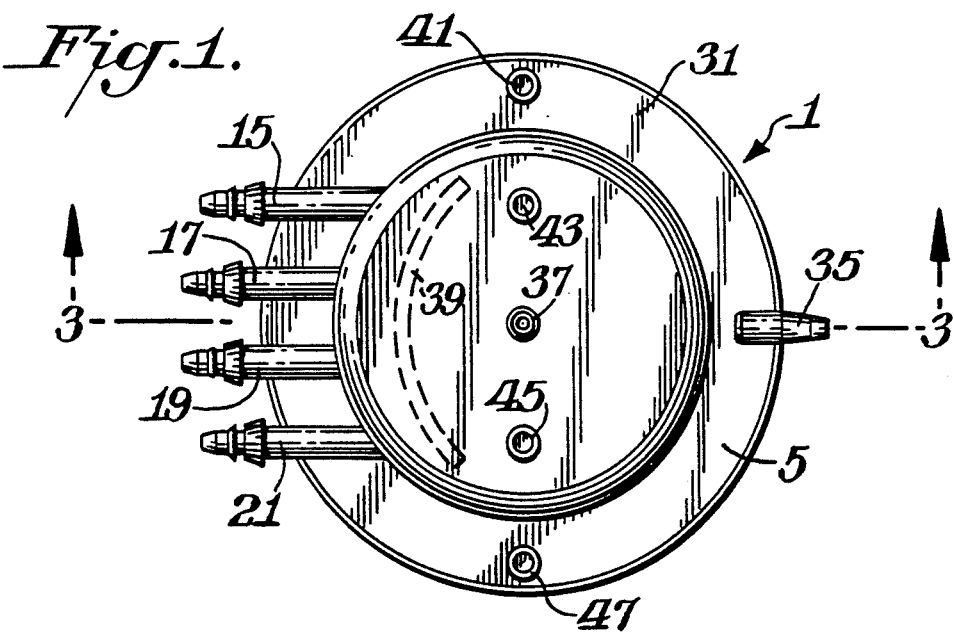
FIG. 1 is a top plan view of an extracorporeal blood treatment and collection device of the invention.
Figure 2:
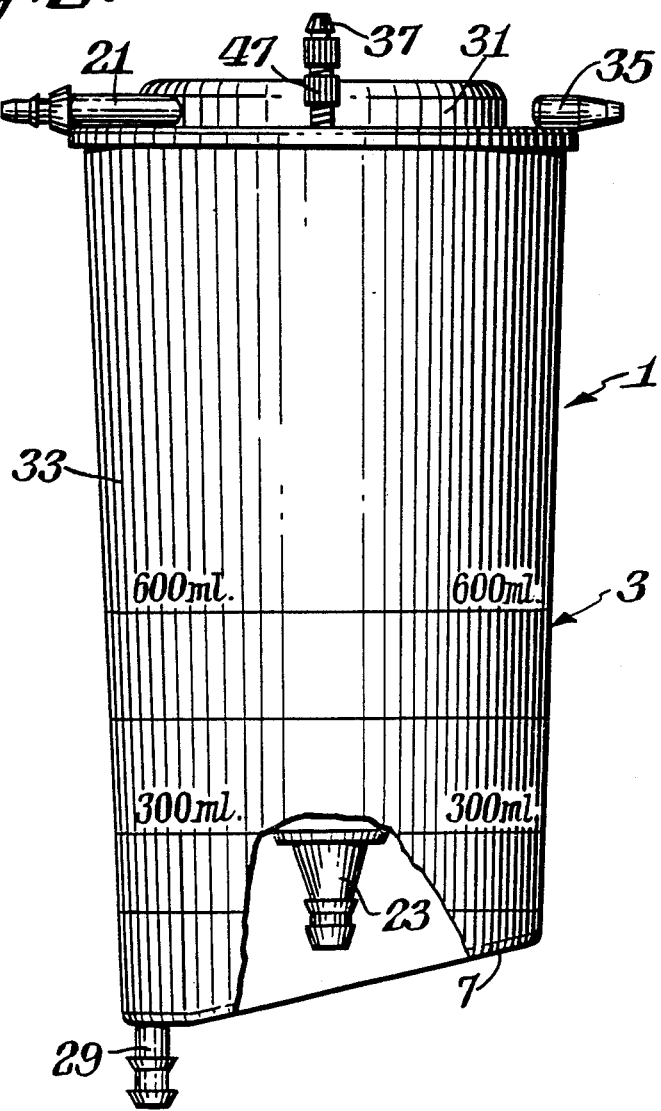
FIG. 2 is a front plan view of the device of FIG. 1 with a portion of the housing broken away.

A disposable blood treatment and collection device 1 of the invention is shown in FIGS. 1 to 5. Device 1 comprises a hollow tubular housing 3 having a top wall 5, a bottom wall 7 and a generally cylindrical side wall 9, a first vertically-extending annular blood treatment element 11, a second vertically-extending annular blood treatment element 13 located directly below element 11, four parallel blood inlets 15, 17, 19 and 21 in communication with the inner space within annular blood treatment element 11, and another blood inlet 23 in communication with the inner space within annular blood treatment element 13. In the normal operation of device 1 one or more lines of tubing conducting cardiotomy blood are connected to one or more of the inlets 15, 17, 19 and 21, and a line carrying the venous return stream is connected to inlet 23. Accordingly, as shown by the arrows in FIG. 3, the cardiotomy blood passes through and is treated by element 11, while the venous return blood passes through and is treated by element 13. The treated cardiotomy blood is combined and collected with the treated venous return blood in a substantially annular reservoir 25, which is defined generally by the bottom and side walls 7 and 9 of housing 3, the annular retaining ring 27 (whose purpose will be discussed below) and the outer peripheries of blood treatment elements 11 and 13. The combined treated cardiotomy and venous return blood is withdrawn from device 1 through a treated blood outlet 29 at the bottom of reservoir 25.

Housing 3 is made of a rigid material that is preferably also transparent. In the preferred embodiment shown in the figures, housing 3 is formed by bonding a generally disc-shaped top cap 31 to a cup-like body portion 33, preferably by solvent bonding or ultrasonic welding. As shown in FIG. 3, side wall 9 is slightly tapered in an upward/outward fashion as a result of the manufacture of portion 33 by injection molding. A graduated scale of markings may be provided on side wall 9 to indicate the volume of treated blood in the reservoir 25 (see FIG. 2). Top cap 31 is preferably manufactured in a single-piece construction including the four inlets 15, 17, 19 and 21, a gas vent 35 (which is in communication with reservoir 25), a central priming port 37, and a curved baffle 39 opposite inlets 15, 17, 19 and 21 whose function is to deflect the blood streams from these horizontal inlets and divert them downwardly. Top cap 31 may also include, in single-piece construction therewith, a plurality of additional ports (e.g. 41, 43, 45 and 47) for the introduction of blood or other fluids upstream or downstream of blood treatment element 11. Likewise, treated blood outlet 29 is preferably in a single-piece construction with the remainder of housing portion 33. On the other hand, in the preferred embodiment shown in the figures blood inlet 23 is not in single-piece construction with housing portion 33 but is instead sealed and bonded to the bottom wall 7 of housing 3 by means of a compression O-ring 49 and a threaded compression ring 51 (see FIG. 3). Ring 51 is screwed and tightened onto an upper threaded portion of inlet 23 with the use of an appropriate tool inserted into groove 54 in ring 51, after which a polyurethane potting compound 53 is injected through apertures (not shown in the figures) in the compression ring 51.

The device 1 shown in the figures also includes three pieces of internal structure incorporated into the design to assist in the proper control and direction of the blood flows through the device. First, a funnel 55, which is bonded (preferably by solvent bonding) to top cap 31, channels the downward flow of blood from inlets 15, 17, 19 and 21 into the inner space within blood treatment element 11. An upper base 65 includes two portions, an elongated generally frusto-conical volume displacing portion 67 (having a rounded upper tip), which prevents an excessive accumulation of untreated blood in the inner space within blood treatment element 11, and a horizontal ring-shaped portion 69 which supports the two innermost annular layers of material in element 11. Additionally, upper base 65 is provided with four vertical perpendicular flow-directing fins 71, 73, 75 and 77. As shown in FIG. 3, the lower rim of funnel 55 is received within steps in these four fins. Finally, a lower base 79 supports the second blood treatment element 13 and in turn sits upon the bottom wall 7 of housing 3. Base 79 includes an inverted cuspate projection 81 that acts to divert the blood flow from inlet 23 in a radially-outward manner. A plurality of slots, e.g. 83, are provided in the frusto-conical wall 85 of lower base 79 to permit blood flow from inlet 23 through blood treatment element 13. Because bases 65 and 79 are non-apertured, blood flow between the inner spaces within annular blood treatment elements 11 and 13 is prevented in device 1. As shown in FIG. 3, the circular corner 66 between portions 67 and 69 of upper base 65 fits within and is bonded to a circular ledge in lower base 79, preferably by solvent bonding.

Blood treatment element 11 comprises an inner annular layer 87 of a porous defoaming material, preferably a reticulated polyurethane foam treated with an antifoam compound such as a silicone antifoam agent and having a pore size of about 20 pores per inch, followed by an annular layer 89 of a non-woven depth filter material, preferably a fibrous polyester depth filter material having a mean pore diameter of about 50 microns, which may be pretreated with a wetting agent. In the device 1 shown in the figures blood treatment element 11 is of the type disclosed in the aforementioned copending U.S. patent application Ser. No. 483,375, which is incorporated herein by reference, and thus also includes an annular layer 91 of a spacer material outside layer 89, preferably a reticulated polyurethane foam untreated with an antifoam agent and having a larger pore size (e.g. about 10 pores per inch) than that in layer 87, followed finally by a thin screen filter 93 having a substantially uniform pore size, preferably a woven nylon or polyester screen having a pore size of about 105 microns. The purpose of the screen filter 93 is to provide a final barrier against the passage of any particulate matter present in the cardiotomy blood, and the layer 91 of spacer material serves to maintain filtering efficiency and prevent excessive pressure drop build-ups during operation by preventing blockage of portions of the screen filter by solid particles trapped in the outer peripheral regions of the depth filter and by providing any gas bubbles remaining in the blood exiting from the depth filter with an opportunity to escape from the liquid blood before coming into contact with and possibly becoming trapped against the screen filter. Screen filter 93 also helps to maintain the structural integrities of blood treatment elements 11 and 13 during operation. Further descriptions of spacer layer 91 and screen filter 93 and the attributes and advantages thereof are given in the aforementioned U.S. patent application Ser. No. 483,375.

As noted earlier the ring-shaped portion 69 of upper base 65 supports and extends beneath the two inner layers, i.e. annular layers 87 and 89, in the first blood treatment element 11. As a result, portion 69 positively prevents blood introduced into device 1 at inlet 23, i.e. the venous return blood, from passing through the layer 89 of depth filter material in treatment element 11. The lower ends of layers 87 and 89 are bonded in a fluid-tight seal to ring-shaped portion 69 of upper base 65, for example with a hot melt adhesive, to prevent the bypass of cardiotomy blood around layers 87 and 89. The upper end of blood treatment element 11 is held against funnel 55, fitting snugly between an annular flange 95 and four vertical perpendicular fins 57, 59, 61 and one not shown in the figures provided on funnel 55. The four fins on funnel 55 may be aligned with fins 71, 73, 75 and 77 on upper base 65. The upper edge of filter screen 93 is bonded between the outer surface of a rigid annular capture ring 97 and the inner surface of the annular flange 95 provided on funnel 55. Ring 97 and flange 95 are bonded together, preferably by solvent bonding.

For facilitating the manufacture of device 1 it is desirable (as shown in the figures) to extend layer 91 and screen 93 to lower base 79, and thus to include this layer and screen in the second blood treatment element 13. This feature of the design of device 1 has no significant adverse effect on the venous return blood introduced through inlet 23 and may in fact enhance the treatment of the venous return blood to some extent. However, the only essential component of the second blood treatment element 13 is the relatively short annular layer 99 of a porous defoaming material held between ring-shaped portion 69 of upper base 65 and lower base 79. It is also essential that second element 13 be free of any depth filter material. The layer 89 of non-woven depth filter material in first element 11 should, of course, have a substantially smaller effective pore size than both of layer 87 in first element 11 and layer 99 in second element 13. Preferably, but not necessarily, layer 99 has the same compositon as layer 87 in blood treatment element 11. Screen filter 93 is bonded in a fluid-tight seal (preferably by solvent bonding) to, and passes between, lower base 79 and a rigid annular retaining ring 27. This bonding and sealing technique is described in detail in the copending, commonly assigned, U.S. patent application Ser. No. 441,464, filed Nov. 15, 1982, now U.S. Pat. No. 4,568,367. The lower edge of screen filter 93 is folded upwardly and tucked between base 79 and bottom housing wall 7. A portion of the bottom housing wall 7 is received in a tight fit by a portion of the annular ring 27, as shown in FIG. 3.

Top cap 31, body portion 33, funnel 55, upper base 65, lower base 79, blood inlet 23 and compression ring 51 are preferably made by conventional methods from a clear plastic material, most preferably a thermoplastic such as a polycarbonate. Retaining ring 27 and capture ring 97 are preferably made by conventional methods from a plastic material, most preferably a thermoplastic such as a polycarbonate. Injection molding of parts is preferred for reasons of cost. The preferred solvents for solvent bonding are dichloromethane, dicfiloroethane and mixtures thereof.

The various elements of device 1 may be readily assembled by conventional methods. Preferably, funnel 55 is first bonded to top cap 31, bases 65 and 79 are bonded together along circular corner 66 and annular layers 87, 89 and 91 and screen filter 93 are preassembled together. The lower portions of layer 91 and screen filter 93 are then temporarily rolled upward and layers 87 and 89 are bonded with a hot melt adhesive to portion 69 of upper base 65. After layer 99 has been pulled over base 79 and inserted into place, retaining ring 27 is bonded to lower base 79 with a portion of screen filter 93 trapped between base 79 and ring 27. Capture ring 97 is then inserted in place between the upper portions of layer 91 and filter screen 93, and base 65 and funnel 55 are then brought together so that the upper ends of layers 87, 89 and 91 abut funnel 55 as shown in FIG. 3 and screen filter 93, flange 95 and ring 97 are in a frictional fit. Capture ring 97 is then bonded to annular flange 95. With inlet 23 already secured in place, lower base 79 is juxtaposed with cup-like body portion 33 and portion 33 is then bonded to top cap 31 to complete the assembly of device 1. After assembly, layers 87, 89 and 91 are snugly held in compression between funnel 55, base 65 and base 79 in the configuration shown in FIG. 3.

During typical operation as a blood treatment and collection device in an extracorporeal blood flow circuit, each of inlets 15, 17, 19 and 21 of device 1 is connected to a line leading from a different cardiotomy suction source, inlet 23 is connected to the venous return line and outlet 29 is connected to a length of tubing leading to an extracorporeal blood pump. Device 1 may be primed, e.g. with sterile saline solution, through central port 37. The gas separated from the inlet streams leaves device 1 through gas vent 35, which is connected to a vent line leading e.g. to a non-pressurized port on an extracorporeal blood oxygenator.

We claim:

1. A device for the treatment and collection of blood from two different sources during a surgical procedure comprising a first vertically-extending annular blood treatment element comprising in series an annular layer of porous defoaming material and an annular layer of non-woven depth filter material, said first annular blood treatment element defining an inner space within itself;

a second vertically-extending annular blood treatment element, located directly below said first element, comprising an annular layer of porous defoaming material, with said second blood treatment element being free of any depth filter material, said second annular blood treatment element defining an inner space within itself;

a hollow housing made of a rigid material and having a top wall, a bottom wall and a generally cylindrical side wall spaced radially outwardly from said first and second blood treatment elements;

a reservoir for collecting treated blood, at least a portion of which is defined by the outer peripheries of the first and second blood treatment elements and the adjacent side housing wall;

a gas vent in the top wall of the housing in communication with said reservoir;

a treated blood outlet in the bottom wall of the housing at the bottom of said reservoir;

a first blood inlet in said housing in communication with the inner space within the first blood treatment element;

a second blood inlet in said housing in communication with the inner space within the second blood treatment element; and means within said housing for providing first and second blood flow paths in the device, said first blood flow path being through the first inlet, the first blood treatment element, the treated blood reservoir and the treated blood outlet, and said second blood flow path being through the second inlet, the second blood treatment element, the treated blood reservoir and the treated blood outlet;

said means including an internal wall within the housing preventing liquid flow between the inner spaces within the first and second blood treatment elements and extending radially outwardly between said elements at least until the outer periphery of the layer of depth filter material in the first element.

2. A device of claim 1 wherein said annular layer of defoaming material in said first blood treatment element is positioned inside said annular layer of non-woven depth filter material.

3. A device of claim 1 wherein at least the side wall of said housing is transparent.

4. A device of claim 1 wherein the side wall of the housing is provided with a graduated scale of markings to indicate the volume of treated blood in said reservoir.

5. A method of treating and combining blood from a first source and blood from a second source during a surgical procedure, comprising the steps of (a) providing a device comprising a first vertically-extending annular blood treatment element comprising in series an annular layer of porous defoaming material and an annular layer of non-woven depth filter material, said first annular blood treatment element defining an inner space within itself;

a second vertically-extending annular blood treatment element, located directly below said first element, comprising an annular layer of porous defoaming material, with said second blood treatment element being free of any depth filter material, said second annular blood treatment element defining an inner space within itself;

a hollow made of a rigid material and having a top wall, a bottom wall and a generally cylindrical side wall spaced radially outwardly from said first and second blood treatment elements;

a reservoir for collecting treated blood, at least a portion of which is defined by the outer peripheries of the first and second blood treatment elements and the adjacent side housing wall;

a gas vent in the top wall of the housing in communication with said reservoir;

a treated blood outlet in the bottom wall of the housing at the bottom of said reservoir;

a first blood inlet in said housing in communication with the inner space within the first blood treatment element;

a second blood inlet in communication with the inner space within the second blood treatment element and means within said housing for providing first and second blood flow paths in the device, said first blood flow path being through the first inlet, the first blood treatment element, the treated blood reservoir and the treated blood outlet, and said second blood flow path being through the second inlet, the second blood treatment element, the treated blood reservoir and the treated blood outlet, said means including an internal wall within the housing preventing liquid flow between the inner spaces within the first and second blood treatment elements and extending radially outwardly between said elements at least until the outer periphery of the layer of depth filter material in the first element;

(b) introducing blood from said first source into the first blood inlet, so that the blood from said first source passes through the first blood treatment element into the treated blood reservoir;

(c) introducing blood from said second source into the second blood inlet, so that the blood from said second source passes through the second blood treatment element into the treated blood reservoir;

(d) collecting and combining treated blood from said two sources in said reservoir; and (e) withdrawing treated and combined blood from said blood outlet.

6. A method of claim 5 wherein the flow rate of blood introduced into said second blood inlet is substantially greater than the flow rate of blood introduced into said first blood inlet.

7. A method of claim 6 wherein the blood stream introduced into the second blood inlet is the venous return stream and the blood stream introduced into the first blood inlet is a cardiotomy blood stream.

* * * * *